United States Patent
Wu

(10) Patent No.: US 10,390,741 B2
(45) Date of Patent: Aug. 27, 2019

(54) METHOD FOR SENSING PHYSIOLOGICAL FEATURE

(71) Applicant: Wistron Corporation, New Taipei (TW)

(72) Inventor: Tung-Ming Wu, New Taipei (TW)

(73) Assignee: Wistron Corporation, New Taipei (TW)

(*) Notice: Subject to any disclaimer, the term of this patent is extended or adjusted under 35 U.S.C. 154(b) by 704 days.

(21) Appl. No.: 14/958,897

(22) Filed: Dec. 3, 2015

(65) Prior Publication Data

US 2017/0095186 A1 Apr. 6, 2017

(30) Foreign Application Priority Data

Oct. 1, 2015 (TW) .............................. 104132412 A

(51) Int. Cl.
*A61B 5/1455* (2006.01)
*A61B 5/024* (2006.01)

(52) U.S. Cl.
CPC .......... *A61B 5/14551* (2013.01); *A61B 5/024* (2013.01); *A61B 5/14552* (2013.01)

(58) Field of Classification Search
CPC . A61B 5/024; A61B 5/14551; A61B 5/14552; G06F 3/0304; G01N 21/474
USPC ................................. 600/300–399; 348/135
See application file for complete search history.

(56) References Cited

U.S. PATENT DOCUMENTS

| | | | |
|---|---|---|---|
| 6,262,798 B1 | 7/2001 | Shepherd et al. | |
| 8,948,832 B2 | 2/2015 | Hong et al. | |
| 2011/0301441 A1* | 12/2011 | Bandic | A61B 5/0059 600/306 |
| 2012/0277559 A1* | 11/2012 | Kohl-Bareis | A61B 5/0261 600/324 |
| 2013/0027545 A1* | 1/2013 | Schwarz | G01N 21/474 348/135 |
| 2014/0378779 A1* | 12/2014 | Freeman | A61B 5/0051 600/301 |

FOREIGN PATENT DOCUMENTS

CN 104207755 12/2014

OTHER PUBLICATIONS

Verkruysse et al. "Remote plethysmographic imaging using ambient light", Optics Express, vol. 16, No. 26, Dec. 2008.*

(Continued)

*Primary Examiner* — Jacqueline Cheng
*Assistant Examiner* — Darin M Janoschka
(74) *Attorney, Agent, or Firm* — JCIPRNET

(57) ABSTRACT

A method for sensing a physiological feature is provided. A sensing apparatus is provided for sensing the physiological feature. The sensing apparatus includes a lighting unit, a light sensing unit, and a controller. The lighting unit and a light sensing unit are located on the same side of a portion under test of a testing subject. The lighting unit transmits a white light to the portion under test. The light sensing unit senses a reflected light. And the controller executes a measurement operation for the physiological feature based on a color wavelength of the reflected light.

3 Claims, 3 Drawing Sheets

(56) References Cited

OTHER PUBLICATIONS

Kohl-Bareis et al., "System for the Measurement of Blood Flow and Oxygenation in Tissue Applied to Neurovascular Coupling in Brain", 2005 Proc. SPIE-OSA Biomed.Optics SPIE 5859:58590F-1-58590F-7.*
Kolarsick et. al, "Anatomy of Physiology of the Skin", Journal of the Dermatolgoy Nurses Association, pp. 203-213.*
"Office Action of Taiwan Counterpart Application," dated Jan. 11, 2017, with English translation thereof, pp. 1-6, in which the listed references were cited.
"Office Action of China Counterpart Application", dated Nov. 28, 2018, pp. 1-8.

* cited by examiner

METHOD FOR SENSING PHYSIOLOGICAL FEATURE

CROSS-REFERENCE TO RELATED APPLICATION

This application claims the priority benefit of Taiwan application serial no. 104132412, filed on Oct. 1, 2015. The entirety of the above-mentioned patent application is hereby incorporated by reference herein and made a part of this specification.

BACKGROUND OF THE INVENTION

1. Field of the Invention

The invention generally relates to a method for sensing a physiological feature, more particularly, to a method for sensing a physiological feature by using a light source irradiation.

2. Description of Related Art

In recent year, with the development of science and technology, portable electronic products have become increasingly popular in daily life, and functions provided thereby have also become increasingly diverse. As a sensor becomes more and more miniaturized, it can be configured on the portable electronic product for detecting a physiological feature of a subject under test. Currently available blood oxygen content sensors and other physiological feature sensors on the market are all clip-on devices. However, these clip-on devices have limitations and can only be applied on fingers, earlobes and so forth, and thereby result in limitations and inconveniences in terms of use.

SUMMARY OF THE INVENTION

The invention is directed to a method for sensing a physiological feature which can increase a convenience in sensing range and increase a precision of a sensing result.

The method for sensing the physiological feature of the invention includes: providing a sensing apparatus for sensing the physiological feature. The sensing apparatus includes a lighting unit, a light sensing unit and a controller. The lighting unit includes a red light source, a green light source and a blue light source, and the lighting unit and the light sensing unit are located on a same side of a portion under test of a testing subject. The lighting unit transmits a first white light to the portion under test, so as to irradiate the first white light to a dermis of the portion under test, wherein the first white light is formed by lights respectively emitted by the red light source, the green light source and the blue light source. The light sensing unit senses a first reflected light, and the controller executes a measurement operation for the physiological feature based on a first color wavelength of the first reflected light.

In one embodiment of the invention, the physiological feature is a blood oxygen content. The method for sensing the physiological feature includes: before transmitting the first white light by the lighting unit, transmitting a second white light to the portion under test, so as to irradiate the second white light to an epidermis of the portion under test, wherein a power of the second white light is smaller than a power of the first white light, and the second white light is formed by lights respectively emitted by the red light source, the green light source and the blue light source; sensing a second reflected light by the light sensing unit; and determining whether a second color wavelength of the second reflected light is within a specified skin color range by the controller.

In one embodiment of the invention, wherein the sensing apparatus is inbuilt with a normal blood oxygen content table and a corrected blood oxygen content table corresponding to the specified skin color range. The method for sensing the physiological feature includes: if the second color wavelength is determined to be within the specified skin color range, then after transmitting the first white light and obtaining the first color wavelength corresponding to the first reflected light, performing a search in the corrected blood oxygen content table based on the first color wavelength by the controller; and if the second color wavelength is determined not to be within the specified skin color range, then after transmitting the first white light and obtaining the first color wavelength corresponding to the first reflected light, performing a search in the normal blood oxygen content table based on the first color wavelength by the controller.

In one embodiment of the invention, the sensing apparatus is inbuilt with a normal blood oxygen content table. The method for sensing the physiological feature includes: if the second color wavelength is determined to be within the specified skin color range, then after transmitting the first white light and obtaining the first color wavelength corresponding to the first reflected light, filtering the first color wavelength based on the second color wavelength by the controller, and performing a search in the normal blood oxygen content table based on the filtered first color wavelength.

In one embodiment of the invention, the method for sensing the physiological feature includes: monitoring a plurality of blood oxygen contents obtained during a scheduled time segment by the controller; and when a change level of the blood oxygen contents is determined to be exceeding a default value, then adjusting the lighting unit to transmit a third white light to the portion under test and issuing a warning message by the controller, wherein a power of the third white light is different from the power of the first white light.

In one embodiment of the invention, after the first reflected light is sensed by the light sensing unit, when the first color wavelength of the first reflected light is abnormal, the lighting unit transmits a colored light to the portion under test, so as to determine whether a non-blood object is being irradiated by a reflected light color of the colored light.

Another method for sensing a physiological feature of the invention includes: providing a sensing apparatus for sensing the physiological feature, wherein the sensing apparatus includes a lighting unit, a light sensing unit and a controller, the lighting unit includes a red light source a green light source and a blue light source, and the lighting unit and the light sensing unit are located on a same side of a portion under test of a testing subject; transmitting a white light to the portion under test by the lighting unit, so as to irradiate the white light to a dermis of the portion under test, wherein the white light is formed by lights respectively emitted by the red light source, the green light source and the blue light source; executing a light source verification procedure to adjust a color of the light source transmitted by the lighting unit; transmitting an adjusted light by the lighting unit to the portion under test; sensing a reflected light of the adjusted light by the light sensing unit; and executing a measurement operation for the physiological feature based on a color wavelength of the reflected light.

In one embodiment of the invention, the step of executing the light source verification procedure includes: obtaining a first color of the reflected light of the white light sensed by the light sensing unit; respectively transmitting a first specified light, a second specified light and a third specified light, wherein the first specified light is the first color, and the second specified light and the third specified light are the lights which have black reflected lights obtained by irradiating the first color; and respectively checking whether the reflected light of the first specified light sensed by the light sensing unit is the first color and whether the reflections lights respectively corresponding to the second specified light and the third specified light are black. If the reflected light of the first specified light is not the first color or one of the reflected light of the second specified light and the third specified light is not black, then the white light is again transmitted to the portion under test to execute the light source verification procedure. If the reflected light of the first specified light is the first color and the reflected lights respectively corresponding to the second specified light and the third specified light are both black, then the lighting unit re-transmits the first specified light to the portion under test. Next, if the reflected light of the re-transmitted first specified light sensed by the light sensing unit is not the first color, then the white light is again transmitted to the portion under test to execute the light source verification procedure; on the contrarily, if the reflected light of the re-transmitted first specified light sensed by the light sensing unit is the first color, then the light source verification procedure is ended, and the lighting unit transmits the adjusted light to the portion under test, wherein the adjusted light is the first specified light.

In one embodiment of the invention, the physiological feature is a blood oxygen content or a heartbeat.

In view of the above, the invention uses the lighting unit and the light sensing unit that are disposed at the same side of the portion under test to sense the physiological feature, so that a sensing range of the sensing apparatus can expand to various parts of the human body. Moreover, by using the red light source, the green light source and the blue light source to produce the white light, the color of the light being transmitted subsequently can be adjusted according to the reflected light color being received, and thus a probability of false determining other human tissues as blood can be lowered.

Several exemplary embodiments accompanied with figures are described in detail below to further describe the invention in details.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

First Embodiment

Figure 1:
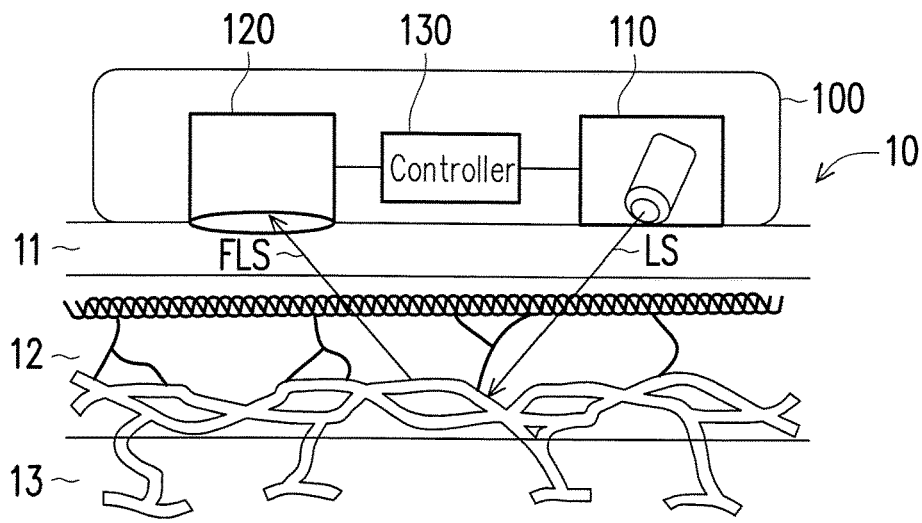
FIG. 1 is a schematic diagram illustrating a sensing apparatus being used to sense a physiological feature of a testing subject according to a first embodiment of the invention.

FIG. 1 is a schematic diagram illustrating a sensing apparatus being used to sense a physiological feature of a testing subject according to a first embodiment of the invention. Referring to FIG. 1, a sensing apparatus 100 includes a lighting unit 110, a light sensing unit 120 and a controller 130. The controller 130 is coupled to the lighting unit 110 and the light sensing unit 120. The controller 130 is, for example, a central processing unit (CPU), a microprocessor, an embedded controlling chip, a digital signal processor (DSP), an application specific integrated circuit (ASIC), or other similar devices. The lighting unit 110 includes a red light source, a green light source and a blue light source. As shown in FIG. 1, the lighting unit 110 and the light sensing unit 120 are located at a same side of portion under test 10 of a testing subject. Herein, the portion under test 10 is an outermost layer of a part of a human body, i.e., skin. The skin can generally be divided into an epidermis 11, a dermis 12 and a hypodermis 13, and blood vessels are distributed in the dermis 11 and the hypodermis 13.

The lighting unit 110 is configured to transmit a light source LS to the portion under test 10. The light sensing unit 120 is configured to receive a reflected light FLS from the portion under test 10. The controller 130 is coupled to the lighting unit 110 and the light sensing unit 120. The controller 130 can control an intensity and a color of the light transmitted by lighting unit 110 and receive a sensing signal of the reflected light from the light sensing unit 12, so as to obtain a color wavelength of the reflected light.

Figure 2:
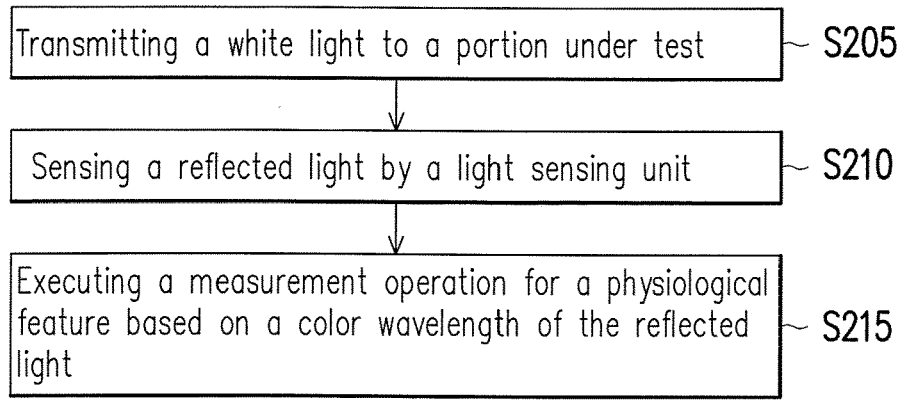
FIG. 2 is flow chart illustrating a method for sensing the physiological feature according to the first embodiment of the invention.

FIG. 2 is flow chart illustrating a method for sensing the physiological feature according to the first embodiment of the invention. Referring to FIG. 1 and FIG. 2, in step S205, the light source LS of a white light is transmitted to the portion under test 10 by the lighting unit 110, so the white light is irradiated to the dermis 12 of the portion under test 10. Herein, the white light is formed by lights respectively emitted by the red light source, the green light source and the blue light source.

Next, in step S210, the light sensing unit 120 senses the reflected light FLS. The light sensing unit 120 can generate a sensing signal according to the reflected light FLS being received. Then, in step S215, the controller 130 executes a measurement operation for the physiological feature based on the color wavelength of the reflected light FLS.

Herein, the physiological feature is, for example, a blood oxygen content or a heartbeat. In terms of measuring the blood oxygen content, the higher the oxygen content in red blood cells, the brighter the red color; on the contrarily, the lower the oxygen content in the red blood cells, the darker the red color. Therefore, the blood oxygen content can be learned by using the color wavelength of the reflected light in coordination with a lookup table. In terms of measuring the heartbeat, by using the reflection of light to calculate a reflection period, a heart rate frequency can further be calculated. Moreover, a variation in blood pressure can also be detected through using the reflection period calculated by the reflection of light. For instance, by detecting a blood pressure based average reflection time and then pre-establishing a comparison table in the sensing apparatus 100, the controller 130 can use the reflection period of the light to estimate whether the blood pressure is rapidly increasing or rapidly decreasing.

In order to increase a precision of sensing, a light source with smaller power can firstly be transmitted to obtain a color wavelength of a skin reflection before executing the measurement operation for the physiological feature, so as to obtain the skin color of the portion under test 10. Moreover, a light source verification procedure can also be firstly performed to adjust the color of the light source transmitted by the lighting unit 110. Respective examples will be provided in the following below.

Second Embodiment

Figure 3:
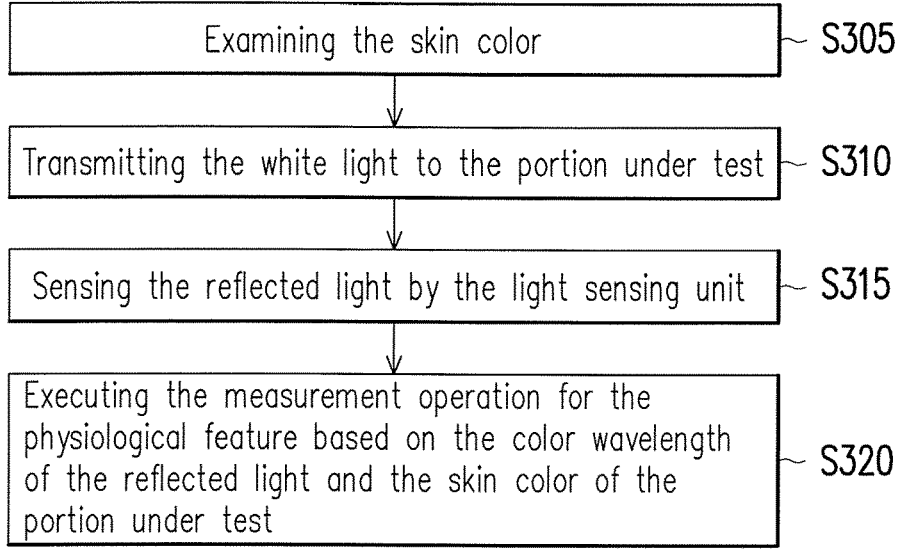
FIG. 3 is flow chart illustrating a method for sensing a physiological feature according to a second embodiment of the invention.

FIG. 3 is flow chart illustrating a method for sensing a physiological feature according to a second embodiment of the invention. Herein, the second embodiment is an extension of the first embodiment and will be described with the sensing apparatus 100 of the first embodiment.

In step S305, the skin color is pre-examined through the sensing apparatus 100. Specifically, the controller 130 controls the lighting unit 110 to transmit a white light with lower power (i.e., a second white light), so the white light only irradiates the epidermis 11 of the portion under test 10. Next, the light sensing unit 120 senses the reflected light (i.e., a second reflected light from the epidermis 11), and the controller 130 determines whether a color wavelength of the second reflected light is within a specified skin color range. Herein, upper and lower limit wavelength values of the specified skin color range can be determined according to various skin colors obtained through statistical calculation. Moreover, a plurality of specified skin color ranges can further be established according to the skin colors of many colored people, respectively.

After obtained the skin color of the portion under test 10, in step S310, the controller 130 controls the lighting unit 110 to transmit a white light with a stronger power (i.e., a first white light), so the white light can be irradiated to the dermis 11 of the portion under test 10. That is to say, the power of the first white light being transmitted in the step S310 is higher than the power of the white light being transmitted in the step S305.

Next, in step S315, the light sensing unit 120 senses a reflected light (i.e., a first reflected light from the dermis 12). In step S320, the controller 130 executes the measurement operation for the physiological feature based on a color wavelength of the first reflected light and the skin color of the portion under test 10. For instance, when measuring the blood oxygen content, the higher the blood oxygen content, the brighter the red color of the reflected light being obtained; and the lower the blood oxygen content, the darker the red color of the reflected light being obtained. Therefore, when measuring the blood oxygen content, different skin colors will cause errors on the results. Accordingly, when measuring the blood oxygen content, different skin colors must be considered to prevent errors.

In the present embodiment, the sensing apparatus 100 is inbuilt with a normal blood oxygen content table and a corrected blood oxygen content table corresponding to the specified skin color range. If the second color wavelength obtained in the step S305 is determined to be within the specified skin color range, then in step S320, the controller 130 performs a search in the corrected blood oxygen content table based on the first color wavelength obtained the step S315. If the second color wavelength is determined not to be within the specified skin color range, then in the step S320, the controller 130 performs a search in the normal blood oxygen content table based on the first color wavelength.

Moreover, the sensing apparatus 100 can be inbuilt with only the normal blood oxygen content table. If the second color wavelength is determined to be within the specified skin color range, then in the step S320, the controller 130 filters the first color wavelength based on the second color wavelength and then performs a search in the normal blood oxygen content table with the filtered first color wavelength.

In addition, the controller 130 can further be used to monitor a plurality of blood oxygen contents obtained during a scheduled time segment. When a change level of the blood oxygen contents is determined to be exceeding a default valued within the scheduled time segment, the controller 130 adjusts the lighting unit 110 to transmit a third white light to the portion under test 10, so as to sense the blood oxygen contents again and to issue a warning message. For instance, "level 1" indicates there is 1 level of level change. Herein, a power of the third white light is different from the power of the first white light that is transmitted in the step S310.

Furthermore, when the first color wavelength of the first reflected light obtained in the step S315 is abnormal (e.g., when the first color wavelength does not belong to a range of red series), the lighting unit 110 transmits a colored light (e.g., a red light, a green light or a blue light) to the portion under test 10, so as to determine whether a non-blood object is being irradiated by a reflected light color of the colored light.

In view of the above, in the second embodiment, by firstly using the white light with smaller power to obtain the skin color of the testing subject, the blood oxygen contents can be determined more accurately.

Third Embodiment

Figure 4:
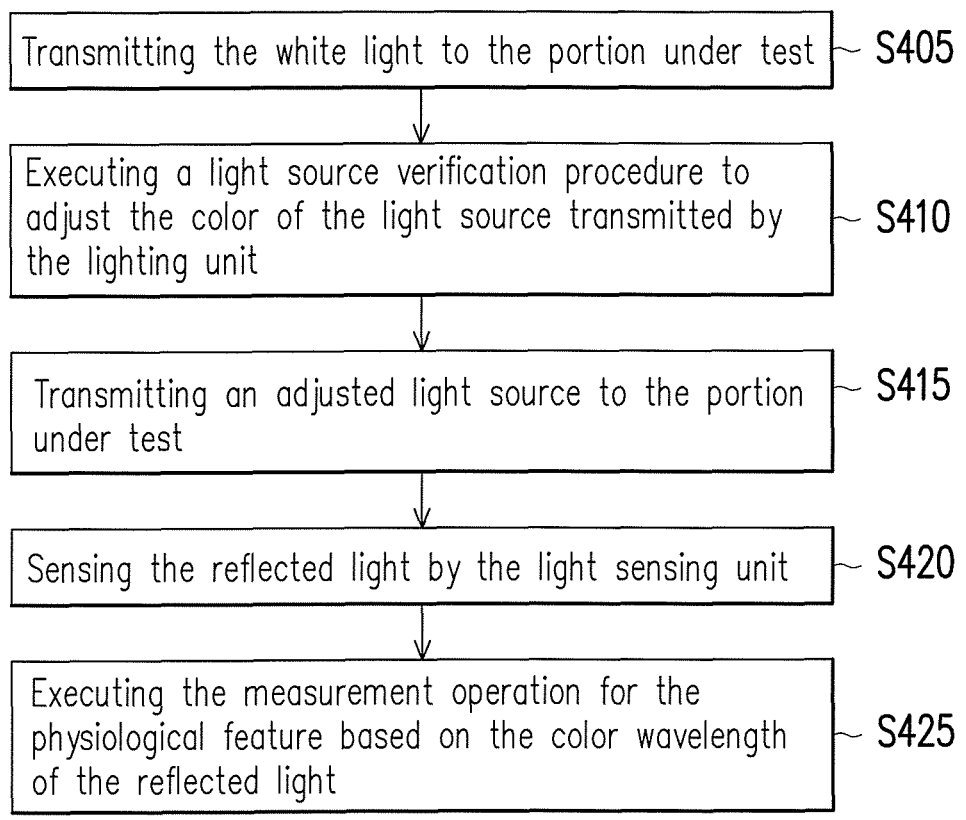
FIG. 4 is flow chart illustrating a method for sensing a physiological feature according to a third embodiment of the invention.

FIG. 4 is flow chart illustrating a method for sensing a physiological feature according to a third embodiment of the invention. Herein, the third embodiment is an extension of the first embodiment and will be described with the sensing apparatus 100 of the first embodiment in the following below.

In step S405, the lighting unit 110 transmits the light source LS, which is a white light, to the portion under test 10, so as to irradiate the white light to the dermis 12 of the portion under test 10. Herein, the white light is formed by lights respectively emitted by the red light source, the green light source and the blue light source.

Next, in step S410, the controller 130 executes the light source verification procedure to adjust the color of the light source transmitted by the lighting unit 110. An example is provided in below to descript the light source verification procedure in detail.

Figure 5:
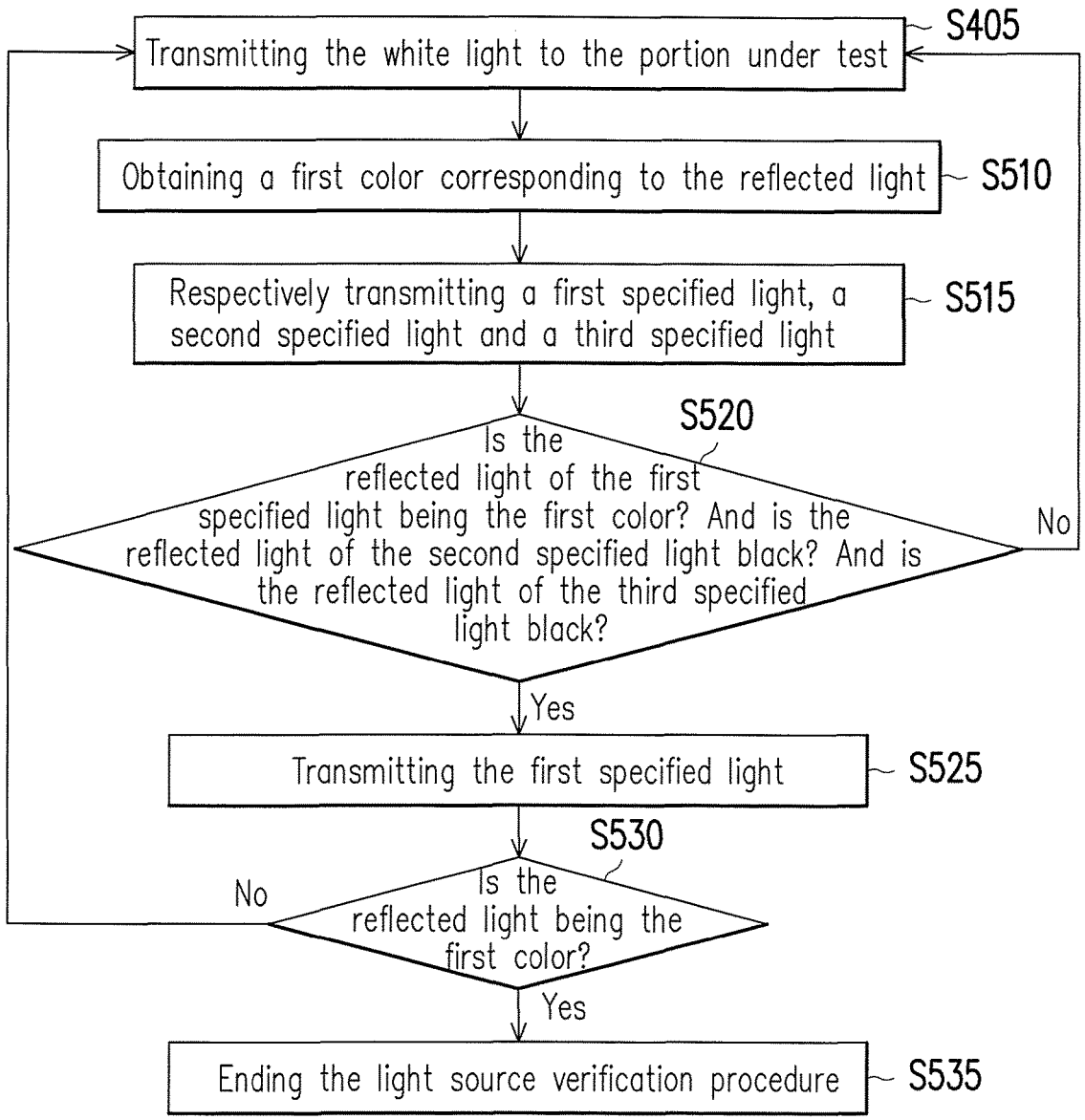
FIG. 5 is flow chart illustrating a light source verification procedure according to the third embodiment of the invention.

FIG. 5 is flow chart illustrating a light source verification procedure according to the third embodiment of the invention. Referring to FIG. 1 and FIG. 5, in step S510, the controller 130 obtains a first color corresponding to the reflected light based on the sensing signal of the light sensing unit 120.

Next, in step S515, a first specified light, a second specified light and a third specified light are respectively transmitted. Herein, the first specified light is the first color, and the second specified light and the third specified light are the lights which have black reflected lights obtained by irradiating the first color. Moreover, in step S520, the reflected light of the first specified light sensed by the light sensing unit 130 is being checked on whether it is the first color, and the second specified light and the third specified light are each being checked on whether the reflected light thereof is black.

If the reflected light of the first specified light is not the first color, the reflected light of the second specified light is not black, or the reflected light of the third specified light is not black, then the step S405 is repeated, and the white light is again transmitted to the portion under test 10 to execute the light source verification procedure.

If the reflected light of the first specified light is the first color and the reflected lights respectively corresponding to the second specified light and the third specified light are both black, then in the step S525, the lighting unit 110 re-transmits the first specified light to the portion under test 10.

Next, in step S530, the reflected light of the re-transmitted first specified light of the step S525 is determined on whether it is the first color. If the reflected light of the first specified light sensed by the light sensing unit 120 is not the first color, then the step S405 is repeated, and the white light is again transmitted to the portion under test 10 to execute the light source verification procedure. If the reflected light of the first specified light sensed by the light sensing unit 120 is the first color, then as shown in step S535, the light source verification procedure is ended, and thus the lighting unit 110 transmits the adjusted light (i.e., the first specified light) to the portion under test 10.

For instance, assuming that the first color obtained at the step S510 is red, then the red light is served as the first specified light. And if the second specified light and the third specified light are, for example, the green light and the blue light, respectively, then the reflected lights obtained when the green light and the blue light are irradiated onto the red color are black. Next, the reflected lights of the red light, the green light and the blue light are being determined on whether they are red, black and black, respectively. If one of the colors does not match, then the white light is transmitted again to perform the detection. If all three colors match, then the red light is being transmitted once again, and if the reflected light being received is still red, then it indicates that a blood vessel instead of other objects is being detected.

Moreover, assuming that the first color obtained at the step S510 is green, then the green light is served as the first specified light. And the second specified light and the third specified light are, for example, the red light and the blue light, respectively. If the reflected lights of the green light, the red light and the blue light are respectively green, black and black, then the green light is transmitted once again; and if the reflected light being received is still green, then the light source verification procedure is ended.

In addition, assuming that the first color obtained at the step S510 is blue, then the blue light is served as the first specified light. And the second specified light and the third specified light are, for example, the green light and the red light, respectively. If the reflected lights of the blue light, the green light and the red light are respectively blue, black and black, then the blue light is transmitted once again; and if the reflected light being received is still blue, then the light source verification procedure is ended. However, the descriptions regarding the first color obtained at the step S510 being green or blue are only provided as examples, and it does not indicate that the blood is green or blue. For instance, if the first color of the reflected light received in the step S510 is dark red, then the first specified light is dark red.

Referring to FIG. 4 again, after the light source verification procedure is ended, in step S415, the controller 130 controls the lighting unit 110 to transmit an adjusted light to the portion under test 10. For instance, assuming that the first specified light obtained at the steps S510 to S530 is dark red, then a dark red light is being irradiated to the portion under test 10.

Then, in step S420, the light sensing unit 120 sense the reflected light. Afterwards, in step S425, the controller 130 executes the measurement operation for the physiological feature based on the color wavelength of the reflected light.

In summary, in the aforementioned embodiments, by using the lighting unit and the light sensing unit that are disposed at the same side of the portion under test to sense the physiological feature, the sensing range of the sensing apparatus can expand to various parts of the human body. Moreover, by sensing the reflected light color while considering the skin color of the testing subject at the same time, the variation in the blood oxygen content can further be determined. In addition, by using the red light source, the green light source and the blue light source to produce the white light, the color of the light being transmitted subsequently can be adjusted according to the received reflected light color, and thus a probability of false determining other human tissues as the blood can be lowered. As such, under a condition that the precision of the blood identification is being increased, the reliability of the measurement for the physiological feature, such as the blood oxygen content, the heartbeat, the blood pressure variation or etc., is also greatly increased.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for sensing a physiological feature, comprising: providing a sensing apparatus for sensing the physiological feature, wherein the sensing apparatus comprises a lighting unit, a light sensing unit and a controller, the lighting unit comprises a red light source, a green light source and a blue light source, and the lighting unit and the light sensing unit are located on a same side of a portion under test of a testing subject;
   transmitting a white light to the portion under test by the lighting unit, so as to irradiate the white light to a dermis of the portion under test, wherein the white light is formed by lights respectively emitted by the red light source, the green light source and the blue light source;
   sensing a reflected light of the white light by the light sensing unit;
   executing a light source verification procedure to adjust a color of the light transmitted by the lighting unit;
   transmitting an adjusted light by the lighting unit to the portion under test;
   sensing a reflected light of the adjusted light by the light sensing unit; and
   executing a measurement operation for the physiological feature based on a color wavelength of the reflected light;
   wherein the step of executing the light source verification procedure comprises:
      obtaining a first color of the reflected light of the white light sensed by the light sensing unit;

respectively transmitting a first specified light, a second specified light and a third specified light, wherein the first specified light is the first color, and the second specified light and the third specified light are the lights which have black reflected lights obtained by irradiating the first color;

respectively checking whether the reflected light of the first specified light sensed by the light sensing unit is the first color and whether the reflected lights respectively corresponding to the second specified light and the third specified light are black;

if the reflected light of the first specified light is the first color and the reflected lights respectively corresponding to the second specified light and the third specified light are both black, re-transmitting the first specified light to the portion under test to adjust the color of the light; and if the reflected light of the first specified light is not the first color or one of the reflected light of the second specified light and the third specified light is not black, re-transmitting the white light to the portion under test to execute the light source verification procedure again.

2. The method for sensing the physiological feature as recited in claim 1,
if the reflected light of the re-transmitted first specified light sensed by the light sensing unit is not the first color, re-transmitting the white light to the portion under test to execute the light source verification procedure again; and if the reflected light of the re-transmitted first specified light sensed by the light sensing unit is the first color, ending the light source verification procedure, and transmitting the adjusted light to the portion under test by the lighting unit, wherein the adjusted light is the first specified light.

3. The method for sensing the physiological feature as recited in claim 1, wherein the physiological feature is a blood oxygen content or a heartbeat.

* * * * *